US012788785B2

(12) United States Patent
Kim et al.

(10) Patent No.: US 12,788,785 B2
(45) Date of Patent: Nov. 10, 2026

(54) PROBIOTICS PREPARATION WITH POTENT PREVENTING EFFECT FROM HANGOVER AND THE PREPARATION METHOD THEREOF

(71) Applicant: VALVET CARE CO., LTD., Seoul (KR)

(72) Inventors: Yong Min Kim, Seoul (KR); Ju Hyun Jeon, Seoul (KR)

(73) Assignee: VALVET CARE CO., LTD., Seoul (KR)

( * ) Notice: Subject to any disclaimer, the term of this patent is extended or adjusted under 35 U.S.C. 154(b) by 240 days.

(21) Appl. No.: 18/611,944

(22) Filed: Mar. 21, 2024

(65) Prior Publication Data

US 2025/0057895 A1 Feb. 20, 2025

(30) Foreign Application Priority Data

Aug. 18, 2023 (KR) ........................ 10-2023-0108245

(51) Int. Cl.

*A61K 35/744* (2015.01)
*A61K 47/14* (2017.01)
*A61K 47/44* (2017.01)
*A61P 25/32* (2006.01)

(52) U.S. Cl.

CPC ............ *A61K 35/744* (2013.01); *A61K 47/14* (2013.01); *A61K 47/44* (2013.01); *A61P 25/32* (2018.01)

(58) Field of Classification Search

None
See application file for complete search history.

(56) References Cited

FOREIGN PATENT DOCUMENTS

| | | | | |
|---|---|---|---|---|
| CN | 112690450 A | 4/2021 | | |
| JP | 2000-004831 A | 1/2000 | | |
| JP | 2011-505354 A | 2/2011 | | |
| JP | 2016-521287 A | 7/2016 | | |
| JP | 2017-043610 A | 3/2017 | | |
| JP | 2018-078887 A | 5/2018 | | |
| JP | 2018-191638 A | 12/2018 | | |
| JP | 2021-508476 A | 3/2021 | | |
| KR | 10-1997-0025405 A | 6/1997 | | |
| KR | 10-2006-0059588 A | 6/2006 | | |
| KR | 10-2006-0065753 A | 6/2006 | | |
| KR | 10-2006-0085086 A | 7/2006 | | |
| KR | 10-2017-0032848 A | 3/2017 | | |
| KR | 10-2078324 B1 | 2/2020 | | |
| KR | 10-2020-0054796 A | 5/2020 | | |
| KR | 10-2021-0083423 A | 7/2021 | | |
| KR | 10-2022-0068518 A | 5/2022 | | |
| KR | 10-2023-0001175 A | 1/2023 | | |
| WO | WO-2012100991 A1 * | 8/2012 | .......... | A23L 33/135 |

OTHER PUBLICATIONS

Swift R et al., "Mechanisms and Mediators", Alcohol Health Res World, 1998; 22: pp. 54-60.
S. Kwon et al., "Effects of Plant Vinegar Extract on the Reduction of Blood Concentration of Alcohol and Acetaldehyde in Alcohol Administrated Rats", The Journal Of Applied Pharmacology, 2005, 13, pp. 107-112.
Hye Mi Jeong et al., "Effects of *Zizyphus jujuba* var. boeunesis Extracts on the Growth of Intestinal Microflora and Its Antioxidant Activities", J. Korean Soc Food Sci Nutr, 2011, 40(4), pp. 500-508.
Manning TS et al., "Prebiotics", Best Practice & Research Clinical Gastroenterology, 2004, vol. 18, No. 2, pp. 287-298.
Cardona et al., "Benefits of polyphenols on gut microbiota and implications in human health", Journal of Nutritional biochemistry, 2013, 24, pp. 1415-1422.
Fuller, R., "Probiotics in man and animals", Journal of Applied Bacteriology, 1989, 66, 365-378.
Roker, E., Alcohol dehydrogenase from bakers yeast, Methods Enzymol, 1955, 1, 500-506.
Tottmar et al., "The subcellular distribution and properties of aldehyde dehydrogenase in rat liver", Biochem. J., 1973, 135, 577-586.
Jeon et al., "Identification and Characterization of Lactic Acid Bacteria Starters Isolated from the Commercial Drink-Yogurt Products", Korean J. Food Sci. Ani. Resour., 2007, vol. 27, No. 4, pp. 509-516.
"Prevent hangovers before you drinking", [online], 2013, Internet <URL: https://web.archive.org/web/20130902210501/http://hangover.hajime123.net/01.html>.
International Search Report of PCT/KR2024/001496 mailed May 7, 2024.
Office Action of Japanese Patent Application No. 2024-057519 mailed Apr. 30, 2025.
Office Action of Korean Patent Application No. 10-2023-0108245 mailed May 13, 2025.

* cited by examiner

*Primary Examiner* — Oluwatosin A Ogunbiyi
(74) *Attorney, Agent, or Firm* — Revolution IP, PLLC

(57) ABSTRACT

A gastric acid-stable probiotic formulation the lactic acid bacteria formulation of the present invention strongly exerts an excellent and advanced effect than the previously known lactic acid bacteria formulation through various experiments, for examples, (1) an experiment for the preparation of an emulsion solution by heating temperature (Experimental Example 1); Alcohol dehydrogenase (ADH) and Aldehyde dehydrogenase (ALDH) activity measurement experiment (Experimental Example 2); *Lactobacillus* viability experiment in artificial gastric juice (pH 2) (Experimental Example 3); Effect of inventive lactic acid bacteria formulation on the relieving hangover symptoms (simple clinical test 1); measurement on the alcohol concentration (%) in exhalation (simple clinical test 2), and it showed an excellent and advanced effect than the previously known lactic acid bacteria preparation in terms of hangover relief effect and liver function improvement effect as well as taste than the previously known lactic acid bacteria preparation.

12 Claims, 4 Drawing Sheets

FIG. 3

| | |
|---|---|
| 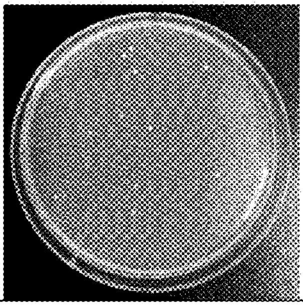 | |
| Artificial Gastric Fluid + [oil(O)+ lactobacillus(L)] Activity in lactobacillus selection medium | $1.2\times10^2$ cfu/g |
| 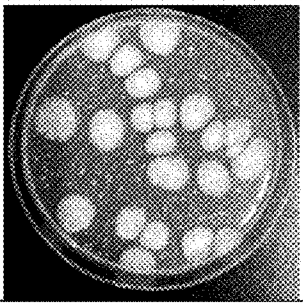 | |
| Artificial Gastric Fluid + [oil(O)+ emulsifier(E)+ lactobacillus(L)] Activity in lactobacillus selection medium | $1.7\times10^3$ cfu/g |
| 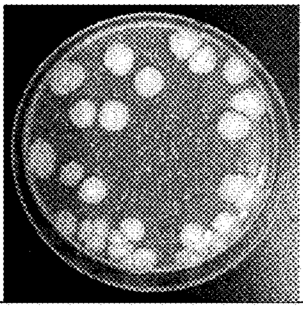 | |
| Artificial Gastric Fluid + [oil(O)+ emulsifier(E)+ lactobacillus(L)+ crushed peanut material(P)] Activity in lactobacillus selection medium | $2.4\times10^3$ cfu/g |

PROBIOTICS PREPARATION WITH POTENT PREVENTING EFFECT FROM HANGOVER AND THE PREPARATION METHOD THEREOF

CROSS REFERENCE TO RELATED APPLICATIONS

This application claims priority to Korean Patent Application No. 10-2023-0108245 filed on Aug. 18, 2023, which is hereby incorporated by reference in its entirety.

BACKGROUND OF THE INVENTION

The present invention relates to a gastric acid-stable probiotic formulation with potent preventing effect from hangover which contains edible oils, nuts and emulsifiers, and the method thereof.

Alcohol acts on the central nervous system of the brain and can temporarily improve mood and forget about suffering, and is used as a means of socializing and as a food for relieving stress. However, hangovers after drinking alcohol are both physical and mental, and the typical symptoms include nausea, vomiting, dizziness, thirst, lethargy, headache, and muscle aches etc (Swift R et al., Alcohol Health Res World 1998; 22: pp. 54-60).

The normal process of ethyl alcohol metabolism is that ethyl alcohol enters the body, is absorbed from the stomach or small intestine, enters the blood vessels, and is transported to the liver. There is alcohol dehydrogenase (ADH) in the liver cells to oxidize the alcohol to acetaldehyde, and the acetaldehyde is decomposed into acetic acid by the acetaldehyde dehydrogenase (ALDH) in the liver cells and transferred to the muscle or adipose tissue of the whole body, and finally decomposed into carbon dioxide gas and water.

Acetaldehyde, which is essential in the metabolic process of ingested alcohol, is the biggest cause of acute alcohol hangover, causing nausea, vomiting, dizziness, thirst, lethargy, and muscle pain, causing socioeconomic losses due to the decrease in work capacity of the general public.

A hangover is a symptom that occurs after drinking alcohol, such as headache, diarrhea, loss of appetite, nausea, vomiting, chills, and night sweats, while objective symptoms include decreased cognition, exercise capacity, hematological changes, and hormonal changes. It is known that the causes of hangovers are dehydration, toxicity of alcohol and alcohol metabolites (acetaldehyde, formaldehyde, acetone, etc.), and nutrient deficiencies (blood sugar, vitamins, mineral deficiencies) due to malabsorption. The severity of hangovers varies greatly depending on individual variations due to genetics and environmental conditions (nutrition, exercise status, degree of dehydration, health status. (S. Kwon et al., The Journal Of Applied Pharmacology, 13 pp 107-112, 2005).

There are about 400 kinds of bacteria present in the human colon and feces, and more than 90% of them are anaerobic strains. They maintain a certain balance and form a microflora in the intestines, and are affected by the health status of the human body, stress, and physiological changes of aging, as well as by food and drugs introduced from the outside. For physical health and life extension, it is necessary to maintain more beneficial bacteria in the intestinal flora and less harmful bacteria.

In 2001, a joint expert committee of the World Health Organization and the World Food Organization defined "probiotics" as live microorganisms that are beneficial to health when consumed in appropriate amounts (Hye Mi Jeong et al., 2011, *J Korean Soc. Food Sci. Nutr.* 40(4), pp. 500-508). This refers to probiotics that can help improve the gut microbiome. On the other hand, prebiotics refer to substances that can be used by useful microorganisms in the intestine and can help the growth and function of beneficial bacteria in the intestine. Non-pulsated polysaccharides and oligosaccharides, which are not easily broken down by human enzymes but can be utilized by microorganisms, have been known as prebiotics till now (Manning TS. Gibson GR. 2004. Prebiotics. Best Practice & Research Clinical Gastroenterology. 18(2): pp. 287-298). Recently, the effects of polyphenols, which can have a beneficial effect on the intestinal microbiota, have become known, and the concept of these prebiotics has been broadened (Cardona et al., 2013, Journal of Nutritional biochemistry, 24, pp 1415-1422).

On the other hand, lactic acid bacteria are representative bacteria that are widely used as probiotics, and they are microorganisms that are widely present in nature and are easily found in the intestines of humans and animals and in fermented foods, and are recognized as safe by the U.S. Food and Drug Administration. Lactic acid bacteria attach to intestinal epithelial cells and parasitize them, thereby improving the properties of intestinal flora, stabilizing intestinal flora, reducing the production of decay products by inhibiting the settlement of harmful bacteria, resulting in various beneficial advantages to host animals, such as prevention of various diseases, immune activation, anti-cancer effects, reducing cholesterol level etc. The reason why lactic acid bacteria have a growth-inhibiting effect on various putrefactive and pathogenic microorganisms is due to several metabolic properties, such as organic acid, hydrogen peroxide, reuterin, diacetyl, acetaldehyde, and bacteriocin as metabolites (Fuller, K., 1989, Probiotics in man and animals, J. Appl. Bacteriol., 66, pp. 365-378) On the other hand, the prior patent literature is as follows.

Korea Patent publication No. 10-2006-0065753 A (Prior art 1) discloses dairy products, health functional foods, and food additives containing strains of the genus *Lactobacillus* with excellent alcohol decomposition are disclosed.

Korea Patent publication No. 10-2017-0032848 A (Prior art 2) discloses novel *Lactobacillus* strains and novelbifidobacterium strains isolated from kimchi or human feces, and their uses to prevent, improve, and treat intestinal damage, liver damage, allergic diseases, inflammatory diseases, and obesity.

Korea Patent publication No. 10-2020-0054796 A (Prior art 3) discloses *Lactobacillus* lactic acid strains with high alcohol dehydrogenase and acetaldehyde dehydrogenase activity.

Korea Patent registration No. 10-2078324 B (Prior art 4) discloses a complex probiotic composition for anti-hangover treatment containing 7 types of *Lactobacillus* of *Lactobacillus plantarum, Lactobacillus casei, Lactobacillus rhamnosus, Lactobacillus acidophilus, Lactococcus lactis, Bifidobacterium breve* and *Bifidobacterium lactis*

Korea Patent publication No. 10-2022-0068518 A (Prior art 5, Applicant name: VALVET CARE CO., LTD.) discloses a composition for inducing voluntary solid preparation intake by a pet. The composition contains unsaturated fatty acid-containing oil, tackifier, sweetener, lactic acid mixture, flavoring agent, preservative, and emulsifier.

Korea Patent publication No. 10-1997-0025405 A (Prior art 6) discloses a *Lactobacillus* preparations of which *Lactobacillus* are not killed by stomach acid and show medicinal activity in the small and large intestine, and the microcapsule preparation of lactic acid bacteria is prepared by the process as follows: apart from the mixture of fat and emulsifier warmed to about 60° C., the two mixed solutions of the protective agent and lactic acid bacteria mixed at about 50° C. is warmed and emulsified at about 60° C., and the emulsification solution is sprayed under high pressure in the cooled dispersion at 4° C. to afford microcapsule preparation of lactic acid bacteria, of which settlement rate of lactic acid bacteria in the intestine increases by preventing the death of lactic acid bacteria by stomach acid, resulting in being effective in improving intestinal health.

Korea Patent publication No. 10-2023-0001175 A (Prior art 7) discloses a complex functionalized enteric-coated soft capsule that contains both high content of lactic acid bacteria and edible oils, while guaranteeing the number of lactic acid bacteria during the shelf life, specifically, a lactic acid bacteria complex for enteric coated soft capsule containing lactic acid bacteria powder 5.0~25.0 wt %, suspension agent 5.0~20.0 wt %, emulsifier 0.5~2.0 wt % and residual edible oil.

Korea Patent publication No. 10-2021-0083423 A (Prior art 8) discloses an oral paste containing about 80~90% oil, about 0.5~20% emulsifier, and about 1~2% probiotic lactic acid bacteria effective against tartar and plaque.

There has been still needed for continuous development of hangover relief compositions that show a higher physical relief effect for headache, heavy feeling, gastrointestinal discomfort, thirst, sweating, and weakness than the existing hangover relief compositions described above.

However, there has been not reported or disclosed about the gastric acid-stable probiotic formulation for hangover relief containing edible oils and emulsifiers and the method thereof in the above cited literatures, the disclosures of which are incorporated herein by reference.

The present inventors have confirmed that the lactic acid bacteria formulation of the present invention strongly exerts an excellent and advanced effect than the previously known lactic acid bacteria formulation through various experiments, for examples, (1) an experiment for the preparation of an emulsion solution by heating temperature (Experimental Example 1); Alcohol dehydrogenase (ADH) and Aldehyde dehydrogenase (ALDH) activity measurement experiment (Experimental Example 2); *Lactobacillus* viability experiment in artificial gastric juice (pH 2) (Experimental Example 3); Effect of inventive lactic acid bacteria formulation on the relieving hangover symptoms (simple clinical test 1); measurement on the alcohol concentration (%) in exhalation (simple clinical test 2), and it showed an excellent and advanced effect than the previously known lactic acid bacteria preparation in terms of hangover relief effect and liver function improvement effect as well as taste than the previously known lactic acid bacteria preparation.

At the result, it has been confirmed that the present invention can provides excellent probiotics and finally, completed the present invention.

SUMMARY OF THE INVENTION

The present invention was developed to overcome the above problems. The present invention is a probiotic formulation comprising lactic acid bacteria, edible oils, and emulsifiers, and it is intended to provide an excellent probiotic formulation that strongly show hangover relief effect, and exert superior and advanced efficacy than previously known *Lactobacillus* preparations in terms of improvement of liver function and palatability and the preparation method thereof The characteristic constitution of the present invention in order to achieve the purpose of the present invention as described above and to realize the characteristic effect of the present invention described below is as follows.

As a preferred embodiment of the present invention, the present invention provides a probiotic formulation for relieving hangovers, which is prepared by the process comprising the steps of (1) heating the edible oil 1 to 90 weight part to 70 to 95° C. and then mixing and stirring the emulsifier to 0.1 to 5 weight part to obtain the mixture of an edible oil and emulsifier at the first step; cooling the mixture and stirring until the temperature is between 2 and 20° C., to obtain a gel-like flocculating mixture at the second stage; slowly injecting 1 weight part of lactic acid bacteria into the gel-shaped flocculation mixture with low-speed stirring to obtain lactic acid bacteria mixture at the third step.

As a further preferred embodiment of the present invention, the present invention provides additional further steps comprising the steps of adding a crushed nut material to the lactic acid bacteria mixture to obtain the nut and lactic acid bacteria mixture at the fourth step; and optionally, adding one or more additional ingredients randomly selected from prebiotics and cohesive agents to provide an inventive probiotic formulation for relieving hangovers.

As a preferred embodiment of the present invention, the above described nut crushed material has a particle size of 0.01 to 0.5 mm, and it is prepared by stirring the crushed nut material at the speed of 30 to 50 rpm to the lactic acid bacteria mixture to obtain the nut and lactic acid bacteria mixture, until all ingredients are evenly mixed for 30 minutes to 3 hours.

As a preferred embodiment of the present invention, the inventive probiotic formulation for relieving hangovers contains (a) lactic acid bacteria, (b) edible oils, and (c) emulsifiers as essential ingredients.

As a preferred embodiment of the present invention, the relative weight ratio of the individual components of the inventive probiotic formulation for relieving hangovers consists of (a) lactic acid bacteria 1.0 weight part, (b) edible oil 1~90 weight part, and (c) emulsifier 0.1~5.0 weight part.

As a preferred embodiment of the present invention, the term "(a) lactic acid bacteria", as defined herein, is characterized by one or more strains selected from microorganisms consisting of the genus *Lactobacillus, Bifidobacterium, Bacillus, Streptococcus*, and *Enterococcus*.

As a desirable embodiment of the present invention, the term "(b) edible oils", as defined herein, are characterized by one or more ingredients selected from a group of avocado oil, canola oil, evening primrose oil, coconut oil, Brazil nut oil, corn oil, cottonseed oil, flaxseed oil, grapeseed oil, hemp oil, olive oil, palm oil, safflower seed oil, soybean oil, peanut oil, sunflower seed oil, krill oil, anchovy oil, salmon oil, rice bran oil, brown rice oil, virgin coconut oil, rosehip oil, and tuna oil.

As a preferred embodiment of the present invention, the term "(c) emulsifiers", as defined herein, are characterized by one or more components selected from a group consisting of propylene glycol fatty acid esters, glycerin fatty acid esters, sucrose fatty acid esters, polyglycerin fatty acid esters, sorbitan fatty acid esters, organic acid monoglycerides, polyoxyethylene fatty acid esters, propylene glycol fatty acid esters, polyoxyethylene fatty acid esters, polysorbate, egg yolk lecithin, soybean lecithin, carboxymethylcellulose, glycerin, soy phospholipids, and stearyl calcium lactate.

As a preferred embodiment of the present invention, the inventive probiotic formulation for relieving hangovers comprises one or more additional ingredients selected from (d) nuts, (e) prebiotics, and (f) cohesive agents in addition to the essential ingredients consisting of (a) lactic acid bacteria, (b) edible oils, and (c) emulsifiers.

As a preferred embodiment of the present invention, the relative weight ratio of the individual components of a probiotic preparation for relieving hangovers consists of (a) lactic acid bacteria 1.0 weight part, (b) edible oil 1~90 weight part, (c) emulsifier 0.1~5.0 weight part, (d) nuts 5.0~90.0 weight part, (e) prebiotics 0.01~5.0 weight part, and (f) cohesive agents 0.1~5.0 weight part.

As a preferred embodiment of the present invention, the term "(d) nuts", as defined herein is characterized by one or more components selected from a group of peanuts, almonds, walnuts, pine nuts, pistachios, pecans, macadamias, hazelnuts, cashews, Brazil nuts, chestnuts, soybeans, cacao nibs, coconuts, sunflower seeds, and pumpkin seeds.

As a preferred embodiment of the present invention, the term "(e) prebiotics", as defined herein, is characterized by being one or more components selected from pentose such as xylose and arabinose, hexose such as glucose, mannose, fructose, and galactose; lactulose, lactitol, sucrose, lactose, maltose, trehalose; fructo-oligosaccharide, raffinose, stachyose, maltodextrin, amylose, amylopectin, starch, cellulose, and pectin.

As a preferred embodiment of the present invention, "(f) the cohesive agents", as defined herein, is characterized by one or more components selected from a group consisting of sodium silico aluminate, xanthan gum, carrageenan, guar gum, diutan gum, cellulose gum, gellan gum, pectin, and carboxymethylcellulose.

Hereinafter, in order to facilitate the implementation of the present invention by a person with ordinary knowledge in the art, the desirable embodiments of the present invention shall be described in detail by referring to the attached drawings.

The inventive probiotic formulation according to the present invention for relieving hangovers is prepared by the process comprising the steps of (1) heating the edible oil 1 to 90 weight part to 70 to 95° C., preferably 75 to 85° C., and then mixing and stirring the emulsifier to 0.1 to 5 weight part to obtain the mixture of an edible oil and emulsifier at the first step; cooling the mixture and stirring until the temperature is between 2 and 20° C., preferably 4 to 10° C., to obtain a gel-like flocculating mixture at the second stage; slowly injecting 1 weight part of lactic acid bacteria into the gel-shaped flocculation mixture with low-speed stirring to obtain lactic acid bacteria mixture at the third step.

Through this process, the emulsifier is dissolved in the heated edible oil, thoroughly mixed, and then cooled to produce a stable gel-like mixture, and then mixed with lactic acid bacteria, which can excellently improve the intestinal retention of lactic acid bacteria.

As a further preferred embodiment of the present invention, the present invention provides additional further steps comprising the steps of adding a crushed nut material to the lactic acid bacteria mixture prepared at $3^{rd}$ step to obtain the nut and lactic acid bacteria mixture at the fourth step; and optionally, adding one or more additional ingredients randomly selected from prebiotics and cohesive agents at the fifth step in addition to the above steps to provide an inventive gastric acid-stable probiotic formulation.

As a preferred embodiment of the present invention, the above described nut crushed material has a particle size of 0.01 to 0.5 mm, preferably, 0.01 to 0.1 mm, and it is prepared by stirring the crushed nut material at the speed of 30 to 50 rpm to the lactic acid bacteria mixture to obtain the nut and lactic acid bacteria mixture, until all ingredients are evenly mixed for 30 minutes to 3 hours.

As a preferred embodiment of the present invention, the inventive probiotic formulation prepared in the fifth step may be sealed under nitrogen gas and stored at 25° C. or below. The inventive probiotic formulation can be controlled below 30° C. and the deterioration of lactic acid bacteria content due to temperature and physical friction can be minimized through low-speed stirring process.

The term "(a) lactic acid bacteria" defined herein means a strain that helps digestion and absorption and inhibits the growth of harmful bacteria in the intestine so that the intestinal environment is in a desirable state, and the form of lactic acid bacteria is not limited thereto, but various forms such as dry powder and dried coarse are preferable, and the size of the strain may be in the range of 0.1~8.0 μm, preferably 0.2~4.0 μm.

In the present invention, the content of individual constituent components is to be expressed as a relative weight part based on the lactic acid bacteria 1 weight part.

The representative strain of the present invention is preferably a random lactic acid bacterium that is widely used as a probiotic, and is readily available in the technical field, such as the American Type Culture Collection (ATCC), the Korean Collection for Type Cultures (KCTC), the Korean Culture Center of Microorganisms (KCCM) affiliated with the Korea Seed Bacteria Association, and the Korean Agricultural Culture Collection (KACC) of the Korean Rural Development Administration.

Specifically, the lactic acid bacterium belonged to genus of *Lactobacillus, Bifidobacterium, Bacillus, Streptococcus*, or *Enterococcus* genus; preferably, *Lactobacillus, Bifidobacterium*, or *Streptococcus* genus, more preferably, *Bifidobacterium*, or *Streptococcus* genus; more specifically, *Bifidobacterium* such as *Bifidobacterium longum, Bifidobacterium bifidum, Bifidobacterium breve, Bifidobacterium animalis* ssp. *lactis, Bifidobacterium adolescentis, Bifidobacterium pseudocatenulatum, Bifidobacterium catenulatum* or *Bifidobacterium infantis, B. thermophilum* species etc;

*Lactobacillus* species such as *Lactobacillus plantarum, Lactobacillus pentosus, Lactobacillus casei, Lactobacillus casei* ssp. *paracasei, Lactobacillus rhamnosus, Lactobacillus acidophilus, Lactobacillus delbrueckii, Lactobacillus delbrueckii* ssp. *bulgaricus, Lactobacillus delbrueckii* ssp. *delbrueckii, Lactobacillus fermentum, Lactobacillus gasseri, Lactobacillus reuteri, Lactobacillus brevis, Lactobacillus cellobiosus, Lactobacillus crispatus, Lactobacillus* GG, *Lactobacillus johnsonii, Lactobacillus lactis, Lactobacillus reuteri, Lactobacillus Salivarius* etc;

*Bacillus* species such as *Bacillus cereus* toyoi or *Bacillus cereus* etc;

*Leuconostoc* species such as *Leuconostoc* citreum, *Leuconostoc mesenteroides* etc.

*Pediococcus* species such as *Pediococcus acidilactici, Pediococcus pentosaceus* etc; *Propionibacterium* species such as *Propionibacterium acidifaciens, Propionibacterium acidipropionici* etc;

*Streptococcus* species such as *Streptococcus thermophilus, Streptococcus cremoris, Streptococcus infantarius, Streptococcus intermedius, Streptococcus lactis, Streptococcus salivarius* subsp. etc;

*Enterococcus* species such as *Enterococcus faecalis* or *Enterococcus faecium* etc;

*Saccharomyces* species such as *Saccharomyces cerevisiae, Saccharomyces boulardii* etc;

More specifically, *Lactobacillus* or *Bifidobacterium* genus strain, more preferably, at least one or two strains selected from the group consisting of *Lactobacillus acidophilus, Lactobacillus rhamnosus* GG, *Lactobacillus plantarum, Bifidobacterium longum, Bifidobacterium animalis* ssp. *Lactis;*

More and more preferably, at least one or two strains selected from the group consisting of *Lactobacillus acidophilus, Lactobacillus rhamnosus* GG, *Lactobacillus plantarum, Bifidobacterium longum* and *Bifidobacterium animalis* ssp. *Lactis.*

The term "(b) edible oils", as defined herein, are characterized by one or more ingredients selected from a group of avocado oil, canola oil, evening primrose oil, coconut oil, Brazil nut oil, corn oil, cottonseed oil, flaxseed oil, grapeseed oil, hemp oil, olive oil, palm oil, safflower seed oil, soybean oil, peanut oil, sunflower seed oil, krill oil, anchovy oil, salmon oil, rice bran oil, brown rice oil, coconut oil, rosehip oil, and tuna oil.

The edible oil is to protect against stomach acid by wrapping the lactic acid bacteria complex. Edible oils are mixed with 1 to 90 weight parts relative to 1 weight part of lactic acid bacteria, preferably mixed with 15 to 30 weight parts.

First of all, the edible oils are heated to 70 to 95° C., preferably to 75 to 85° C., and then the heated edible oil is stirred with an emulsifier until the temperature of the mixture is reached to 2 to 20° C., preferably 4 to 10° C., in a circulating cooling water bath maintained at 0 to 10° C., preferably 0 to 5° C., to form a gel-like stable flocculating mixture.

The term "(c) emulsifiers", as defined herein, are characterized by one or more components selected from a group consisting of propylene glycol fatty acid esters, glycerin fatty acid esters, sucrose fatty acid esters, polyglycerin fatty acid esters, sorbitan fatty acid esters, organic acid monoglycerides, polyoxyethylene fatty acid esters, propylene glycol fatty acid esters, polyoxyethylene fatty acid esters, polysorbate, egg yolk lecithin, soybean lecithin, carboxymethylcellulose, glycerin, soy phospholipids, and stearyl calcium lactate.

The emulsifier is to play a role in increasing the miscibility between the compositions in the lactic acid bacteria complex, and after heating the edible oil to 70 to 95° C., preferably 75 to 85° C., when the emulsifier is mixed, the emulsifier is melted, and the mixability with edible oils is greatly increased.

Conventionally, the process of mixing the emulsifier by heating the edible oil to 60° C. has been known, but there has been some needs to dissolve them thoroughly since the emulsifier could not mixed with the edible oil thoroughly although the edible oil and emulsifier are heated to 60° C.

The present inventors have found that been that the edible oil shall be heated to at least 70° C. in order to dissolving the emulsifier in the edible oil, and if the edible oil is heated to more than 100° C., there is a possibility of acidification. Therefore, it has been confirmed that it is preferable to heat the edible oil to a temperature of 75 to 85° C. to dissolve an emulsifier (See FIG. 1).

The content of emulsifier can be included in the 0.1~5.0 weight part, preferably, 0.20~1.60 weight part, more preferably 0.30~1 weight part based on lactic acid bacterial weight part.

At this time, if the emulsifier content is less than 0.1 weight part, there may be some problem of poor miscibility with lactic acid bacteria mixed powder and edible oil, and even if it is used in excess of 5.0 weight part, there is no longer an increase in miscibility between compositions, so it is appropriate to use it within the above range.

As a preferred embodiment of the present invention, the inventive probiotic formulation for relieving hangovers contains (a) lactic acid bacteria, (b) edible oils, and (c) emulsifiers as essential ingredients.

As a preferred embodiment of the present invention, the relative weight ratio of the individual components of the inventive probiotic formulation for relieving hangovers consists of (a) lactic acid bacteria 1.0 weight part, (b) edible oil 1~90 weight part, and (c) emulsifier 0.1~5.0 weight part.

Among these, the detailed descriptions on (a) lactic acid bacteria, (b) edible oils and fats, and (c) emulsifiers are omitted as they have been fully detailed above.

As a preferred embodiment of the present invention, the inventive probiotic formulation for relieving hangovers comprises one or more additional ingredients selected from (d) nuts, (e) prebiotics, and (f) cohesive agents in addition to the essential ingredients consisting of (a) lactic acid bacteria, (b) edible oils, and (c) emulsifiers.

As a preferred embodiment of the present invention, the relative weight ratio of the individual components of a probiotic formulation for relieving hangovers consists of (a) lactic acid bacteria 1.0 weight part, (b) edible oil 1~90 weight part, (c) emulsifier 0.1~5.0 weight part, (d) nuts 5.0~90.0 weight part, (e) prebiotics 0.01~5.0 weight part, and (f) cohesive agents 0.1~5.0 weight part.

As a more preferred embodiment of the present invention, the relative weight ratio of the individual components of a probiotic formulation for relieving hangovers consists of (a) lactic acid bacteria 1.0 weight part, (b) edible oil 10~30 weight part, (c) emulsifier 0.2~1.6 weight part, (d) nuts 15.0~75.0 weight part, (e) prebiotics 0.1~2.0 weight part, and (f) cohesive agents 1.0~4.0 weight part.

As a preferred embodiment of the present invention, the term "(d) nuts", as defined herein is characterized by one or more components selected from a group of peanuts, almonds, walnuts, pine nuts, pistachios, pecans, macadamias, hazelnuts, cashews, Brazil nuts, chestnuts, soybeans, cacao nibs, coconuts, sunflower seeds, and pumpkin seeds as an additive to form a suitable viscosity of the composition, to increase the flavor/texture, and further to enhance the activity of lactic acid bacteria.

The nuts containing a large amount of unsaturated fatty acids, are essential ingredients that play a beneficial role in various healthy effect including blood circulation improvement, and the nuts are preferable in the form of a crushed nut material, and the suitable particle size of the crushed nut material is 0.01 to 0.5 mm, preferably 0.01 to 0.1 mm to the extent that it shows a paste shape.

The content of nuts is mixed in the 5.0 to 90.0 weight part based on lactic acid bacteria 1 weight part, preferably 15.0 to 75.0 weight based on lactic acid bacteria 1 weight part.

The present inventors have found that nuts not only improve the palatability and organolepcy of probiotic formulation, but also have an excellent effect on maintaining the viability of lactic acid bacteria in stomach acid through several experiments.

As a preferred embodiment of the present invention, the inventive gastric acid-stable probiotic formulation comprises one or more additional ingredients selected from (e) prebiotics, and (f) cohesive agents in addition to the above essential ingredients.

The term, "(e) prebiotics" defined herein are used as food for lactic acid bacteria, and are not digested by the digestive tract enzymes of animals, but proliferate lactic acid bacteria such as bifidobacteria, which are intestinal bacteria, in the lower part of the small intestine, and exhibit various physiological effects including intestinal action, which comprise monosaccharides, disaccharides, oligosaccharides, and polysaccharides etc as well-known prebiotics in the sugar industry, preferably pentose such as xylose and arabinose etc; hexose such as glucose, mannose, fructose, and galactose; disaccharides such as lactulose, lactitol, sugar, lactose, maltose, and trehalose; oligosaccharides, such as fructo-oligosaccharides, raffinose, stachyose, and maltodextrin; polysaccharides such as amylose, amylopectin, starch, cellulose, and pectin; more preferably, glucose, fructose, galactose, sucrose, lactose, fructo-oligosaccharide, etc., more and more preferably, glucose, fructose, lactulose, lactitol, or fructo-oligosaccharides The content of (e) prebiotics can be added or reduced to a dose well-known in the art according to the type and content of (a) lactic acid bacteria, and it is desirable to put 0.01 to 5 weight parts, preferably 0.1 to 2.0 weight parts, based on lactic acid bacteria 1 weight part.

The term, "(f) the cohesive agents", as defined herein contains 0.1 to 5 weight parts, preferably, 1 to 4 weight parts, compared to 1 weight of lactic acid bacteria, and serves to give viscosity to the composition, which is preferably one or more components selected from a group consisting of sodium silico aluminate, xanthan gum, carrageenan, guar gum, diutan gum, cellulose gum, gellan gum, pectin, and carboxymethylcellulose.

If the content of the cohesive agents is less than 0.1 weight part, the effect is insignificant, and if the content of the cohesive agents exceeds 5 weight part, the viscosity may increase excessively and the workability may decrease.

In addition, the present invention can additionally add one or more additives selected in the appropriate amount of color, fragrance, etc., to the composition in the range of about 0~10 weight parts compared to the total lactic acid bacteria 1 weight part.

Accordingly, it is an object of the present invention to provide a pharmaceutical composition, a health functional food, a health care food, a dietary supplement or food additives comprising the probiotic formulation prepared by the above-described process to treat or prevent hangover or liver disease.

The term, "liver disease" as defined herein includes autoimmune liver disease, drug-induced liver disease, alcoholic liver disease, non-alcoholic liver disease, infectious liver disease, congenital metabolic liver disease, acute hepatitis, chronic hepatitis, liver cirrhosis, liver sclerosis, fatty liver or liver cancer, preferably, alcoholic liver disease or non-alcoholic liver disease The present inventors have confirmed that the lactic acid bacteria formulation of the present invention strongly exerts an excellent and advanced effect than the previously known lactic acid bacteria formulation through various experiments, for examples, (1) an experiment for the preparation of an emulsion solution by heating temperature (Experimental Example 1); Alcohol dehydrogenase (ADH) and Aldehyde dehydrogenase (ALDH) activity measurement experiment (Experimental Example 2); *Lactobacillus* viability experiment in artificial gastric juice (pH 2) (Experimental Example 3); Effect of inventive lactic acid bacteria formulation on the relieving hangover symptoms (simple clinical test 1); measurement on the alcohol concentration (%) in exhalation (simple clinical test 2), and it showed an excellent and advanced effect than the previously known lactic acid bacteria preparation in terms of hangover relief effect and liver function improvement effect as well as taste than the previously known lactic acid bacteria formulation.

In order to solve the above purpose, the present invention provide a pharmaceutical composition comprising the inventive probiotic formulation as an active ingredient to treat or prevent hangover or liver disease.

The present invention provide a health functional food comprising the inventive probiotic formulation as an active ingredient to prevent or alleviate hangover or liver disease.

The inventive composition may comprises the above probiotic formulation as 0.01~99%, by weight based on the total weight of the composition.

However, the above composition is not necessarily limited to thereto, but may change depending on the patient's condition and the type and progression of the disease.

The composition according to the present invention can be provided as a pharmaceutical composition containing pharmaceutically acceptable carriers, adjuvants or diluents.

Pharmaceutical preparations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

Pharmaceutically acceptable carriers, adjuvants or diluents such as lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, magnesium stearate and mineral oil etc may be used herein.

The preparations may additionally include fillers, anti-agglutinating agents, lubricating agents, wetting agents, flavoring agents, emulsifiers, preservatives and the like.

In the case of preparations, it is prepared using diluents or excipients such as fillers, extenders, binders, humectants, disintegrators, surfactants, etc.

Solid preparations for oral administration include tablets, pills, powders, granules, capsules, etc., and these solid formulation are prepared by mixing the inventive formulation with at least one excipient selected from starch, calcium carbonate, sucrose or lactose, gelatin, etc. In addition to simple excipients, lubricants such as magnesium stearate, talc are also used.

Liquid type oral preparations of the present invention include suspensions, liquids, emulsions, syrups, etc., and may include various excipients, such as humectants, sweeteners, fragrances, and preservatives in addition to water and liquid paraffin, which are commonly used simple thinners.

Preparations for parenteral administration include sterile aqueous solutions, non-aqueous solvents, suspensions, emulsions, lyophilized preparations, and suppositories. Non-aqueous solvents and suspensions may include olive oil such as propylene glycol, polyethylene glycol, vegetable oils and injectable esters such as ethyl oleate. Suppositories such as witepsol, macrogol, tween 61, cacao, lauringe, glycerozeratin, etc. may be used.

The desirable dose of the inventive probiotic formulation varies depending on the condition and the weight of the subject, severity, drug form, route and period of administration, and may be chosen by those skilled in the art. However, in order to obtain desirable effects, it is generally recommended to administer at the amount ranging from 0.01 to 10 g/kg preferably, 1 mg/kg to 1 g/kg by weight/day of the inventive probiotic formulation of the present invention. The dose may be administered in single or divided into several times per day. Therefore, the above dosage does not in any way limit the scope of the invention.

The pharmaceutical composition of present invention can be administered to a subject animal such as mammals (rat, mouse, domestic animals or human) via various routes. All modes of administration are contemplated, for example, administration can be made orally, rectally or by intravenous, intramuscular, subcutaneous injection, etc.

In accordance with another aspect of the present invention, there is also provided a method of treating or preventing hangover or liver disease, wherein the method comprises administering a composition comprising a therapeutically effective amount inventive probiotic formulation, into the mammal suffering from hangover or liver disease.

In accordance with another aspect of the present invention, there is also provided a use of a composition comprising inventive probiotic formulation, for manufacture of medicines employed for treating or preventing hangover or liver disease.

Accordingly, it is the other object of the present invention to provide a health functional food comprising a therapeutically effective amount of the inventive probiotic formulation for the prevention or alleviation of hangover or liver disease.

The inventive composition may comprises above probiotic formulation as 0.01~99%, by weight based on the total weight of the composition.

However, the above composition is not necessarily limited to thereto, but may change depending on the patient's condition and the type and progression of the disease.

The composition according to the present invention can be provided as a pharmaceutical composition containing pharmaceutically acceptable carriers, adjuvants or diluents.

Pharmaceutical preparations containing present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

Pharmaceutically acceptable carriers, adjuvants or diluents such as lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, magnesium stearate and mineral oil etc may be used herein.

The preparations may additionally include fillers, anti-agglutinating agents, lubricating agents, wetting agents, flavoring agents, emulsifiers, preservatives and the like.

In the case of preparations, it is prepared using diluents or excipients such as fillers, extenders, binders, humectants, disintegrators, surfactants, etc.

Solid preparations for oral administration include tablets, pills, powders, granules, capsules, etc., and these solid formulation are prepared by mixing the inventive formulation with at least one excipient selected from starch, calcium carbonate, sucrose or lactose, gelatin, etc. In addition to simple excipients, lubricants such as magnesium stearate, talc are also used.

Liquid type oral preparations of the present invention include suspensions, liquids, emulsions, syrups, etc., and may include various excipients, such as humectants, sweeteners, fragrances, and preservatives in addition to water and liquid paraffin, which are commonly used simple thinners.

Preparations for parenteral administration include sterile aqueous solutions, non-aqueous solvents, suspensions, emulsions, lyophilized preparations, and suppositories. Non-aqueous solvents and suspensions may include olive oil such as propylene glycol, polyethylene glycol, vegetable oils and injectable esters such as ethyl oleate. Suppositories such as witepsol, macrogol, tween 61, cacao, lauringe, glycerogelatin, etc. may be used.

The desirable dose of the inventive probiotic formulation varies depending on the condition and the weight of the subject, severity, drug form, route and period of administration, and may be chosen by those skilled in the art. However, in order to obtain desirable effects, it is generally recommended to administer at the amount ranging from 0.01 mg/kg to 10 g/kg preferably, 1.0 mg/kg to 1 g/kg by weight/day of the inventive probiotic formulation of the present invention. The dose may be administered in single or divided into several times per day. Therefore, the above dosage does not in any way limit the scope of the invention.

Accordingly, it is the other object of the present invention to provide a health functional food comprising the inventive probiotic formulation for the prevention or alleviation of hangover or liver disease.

The term "a functional health food" defined herein" the functional food having enhanced functionality such as physical functionality or physiological functionality by adding the inventive formulation of the present invention to conventional food to prevent or improve the purposed diseases in human or mammal, which is stipulated by Korean functional health food Law No. 6727.

The inventive functional health food may comprises above probiotic formulation as 0.01~95%, preferably, 1~80% by weight based on the total weight of the composition.

Furthermore, the composition of the present invention may be a health care food for the purpose of treating or hangover or liver disease.

In addition, for the purpose of preventing and improving hangover or liver disease, it can be manufactured and processed as health functional foods in the form of pharmaceutical administrations such as acids, granules, tablets, capsules, pills, suspensions, emulsions, syrups, etc., or in the form of tea agents, leached teas, and health drinks etc.

Accordingly, it is the other object of the present invention to provide a health care food or diet supplement comprising an inventive probiotic formulation for the prevention or alleviation of hangover or liver disease.

The main ingredient in a health care food as defined herein means that the content of the active ingredient relative to the weight of the total composition is in the range of approximately 30% to 99%, preferably in the range of 50% to 99%, and preferably in the range of 70% to 99%.

Providing that the health beverage composition of present invention contains above described formulation(s) as an essential component in the indicated ratio, there is no particular limitation on the other liquid component, wherein the other component can be various deodorant or natural carbohydrate etc such as conventional beverage. Examples of aforementioned natural carbohydrate are monosaccharide such as glucose, fructose etc; disaccharide such as maltose, sucrose etc; conventional sugar such as dextrin, cyclodextrin; and sugar alcohol such as xylitol, and erythritol etc. As the other deodorant than aforementioned ones, natural deodorant such as taumatin, stevia extract such as levaudiosideA, glycyrrhizin et al., and synthetic deodorant such as saccharin, aspartam et al., may be useful favorably. The amount of above described natural carbohydrate is generally ranges from about 0 to 20 g in the ratio of 100 mℓ of present beverage composition.

In addition, the probiotic preparation of the present invention may be added to food or beverage for the purpose of preventing hangover or liver disease. At this time, the amount of the probiotic formulation in food or beverage can be added from 0.01 to 15% by weight of the total food weight, and the health drink composition can be added in a ratio of 0.02 to 5 g, preferably 0.3 to 1 g based on 100 ml.

Accordingly, it is the other object of the present invention to provide a food or food additive comprising an inventive probiotic formulation for the prevention or alleviation hangover or liver disease.

The items listed in the "Food Additives Code" include, for example, chemically synthesized products such as ketones, glycine, potassium citrate, nicotinic acid, cinnamic acid, persimmon coloring, licorice extract, crystalline cellulose, guar gum, etc., mixed preparations such as L-monosodium glutamate, noodle additive alkaline agents, preservatives, and tar pigment preparations.

Functional health foods containing probiotic preparations of the present invention include bread, rice cakes, dried fruits, candy, chocolates, chewing gum, confectionery such as jams, ice cream, ice cream, ice cream products, ice cream products, milk products, low-fat milk, lactose-lyzed milk, processed milk, goat milk, fermented milk, butter oil, concentrated milk, milk cream, natural cheese, processed cheese, milk powder, processed milk products such as whey, processed meat products, processed egg products, meat products such as hamburgers, fish meat products such as fish cakes, ham, sausage, bacon, etc. Noodles such as yutang noodles, luxurious dried noodles, modified noodles, frozen noodles, pasta fruits, vegetable drinks, carbonated drinks, lactic acid bacteria drinks such as soy milk, yogurt, and mixed drinks Soy sauce, soybean paste, red pepper paste, chunjang, cheonggukjang, mixed paste, vinegar, sauces, tomato ketchup, curry, seasonings such as dressing, margarine, shortening and pizza are not limited to.

In the process of manufacturing the health functional food, the content of the probiotic formulation according to the present invention added to the food including the beverage can be appropriately added or subtracted as necessary.

As described in the present invention, the present inventors have confirmed that the lactic acid bacteria formulation of the present invention strongly exerts an excellent and advanced effect than the previously known lactic acid bacteria formulation through various experiments, for examples, (1) an experiment for the preparation of an emulsion solution by heating temperature (Experimental Example 1); Alcohol dehydrogenase (ADH) and Aldehyde dehydrogenase (ALDH) activity measurement experiment (Experimental Example 2); *Lactobacillus* viability experiment in artificial gastric juice (pH 2) (Experimental Example 3); Effect of inventive lactic acid bacteria formulation on the relieving hangover symptoms (simple clinical test 1); measurement on the alcohol concentration (%) in exhalation (simple clinical test 2), and it showed an excellent and advanced effect than the previously known lactic acid bacteria preparation in terms of hangover relief effect and liver function improvement effect as well as taste than the previously known lactic acid bacteria preparation.

Therefore, the present invention can provides the therapeutics or functional health food for treating and preventing hangover or liver disease.

BRIEF DESCRIPTION OF THE DRAWINGS

The above and other objects, features and other advantages of the present invention will more clearly understood from the following detailed description taken in conjunction with the accompanying drawings, in which;

FIG. 3 represents the test result of *Lactobacillus* viability experiment in artificial gastric juice (pH 2).

DETAILED DESCRIPTION OF THE INVENTION

Figure 1:
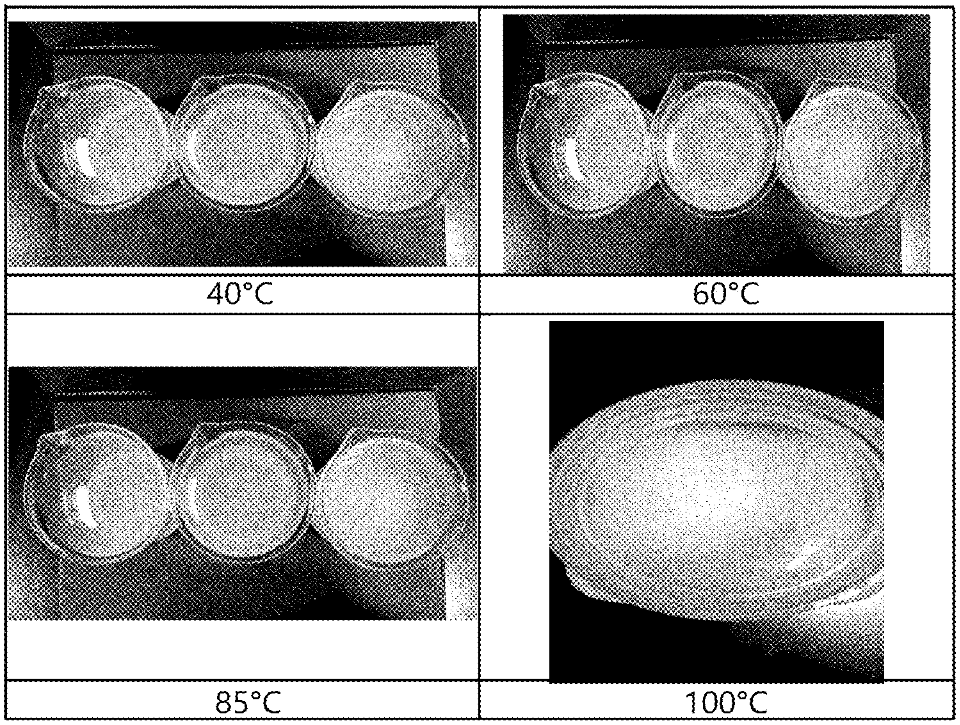
FIG. 1 shows the experimental results of observing the emulsion properties of the emulsifier of the present invention by various temperatures.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Reference Example, Examples and Experimental Examples are intended to further illustrate the present invention without limiting its scope.

Example 1. Preparation of Inventive Emulsifier-Added Lactic Acid Bacteria Formulation (Composition: Table 1)

20 g of sunflower oil (vegetable oil, Sajo Daelim Co., Ltd.) was poured into a stirring heater (Hotplate Stirrer. MSH-20D) and heated to 75 to 85° C.

0.4 g of glycerin fatty acid ester (emulsifier, ES food ingredient) was added thereto with stirring.

The mixture of vegetable oil and emulsifier obtained by the above stage were emulsified by stirring until the temperature of the mixture was 4 to 10° C. in a circulating cooling tank (SH-WB-7CDR) maintained at 0 to 4° C. (Test-1: Preparation of emulsion solution according to various temperature, 40° C., 60° C., 85° C., 100° C. and the test results refer to Experimental Example 1)

*Lactobacillus acidophilus* DDS-1 (Olab), *Lactobacillus rhamnosus* GG (Alllab), *Lactobacillus plantarum* VI-07 (Vitech Co., Ltd.) mixed into the emulsified oil formed in the form of a gel. *Bifidobacterium longum* BL5 (Vitech Co., Ltd.) and *Bifidobacterium animalis* (*Bifidobacterium animalis* ssp. *lactis* BLC1) were evenly mixed at the same rate (2×109 cfu/g) respectively and 1 g of mixed lactic acid bacteria were used in the experiment (Test-2: the experimental method for process the observation of the viability of lactic acid bacteria and experimental results in artificial gastric solution (pH 2) refer to the following Experimental Example 2.)

Peanuts (nuts, DaeChang Foods Co. Ltd), which contains natural sweeteners such as fructooligosaccharides (feed for lactic acid bacteria; prebiotics) and unsaturated fatty acids as additives to form suitable viscosity of the composition, increase flavor/texture, further enhance the activity of lactic acid bacteria and provides beneficial effect such as improved blood circulation etc, were added thereto and stirred with a mixing stirrer (OFM-1507B, Opel Co., Ltd.) at a speed of 30 to 50 rpm for more than 1 hour until all the ingredients were evenly mixed.

At this time, in the case of nuts, it is best to grind them with a crushing device (ultra-high-speed vacuum blender, KCB-001W, Kucharm Co., Ltd.) so that the particle size is 0.01~0.1 millimeters (mm) (the degree to which the paste shape is visible). (Test-3: the peanut was chosen among peanuts, almonds, and walnuts by the evaluation test according to various criteria such as throat clearing and palatability and test result refer to Experiment Example 3)

TABLE 1

| Composition of lactic acid formulation | | | |
|---|---|---|---|
| Formulation* | Composition A | Composition B | Composition C |
| Olive oil | 20 g | 20 g | 95.5 g |
| Emulsifier | 0.3 g | — | 1.5 g |
| Fructo-oligosaccharide | 1 g | 1 g | 1 g |
| crushed nut material | 76.7 g | 77 g | — |
| mixed lactic acid bacteria | 2 g | 2 g | 2 g |
| sum | 100 g | 100 g | 100 g |

*Composition A: Olive oil + Emulsifier + Fructo-oligosaccharide + crushed nut material + mixed lactic acid bacteria /
Composition B: Olive oil + Fructo-oligosaccharide + crushed nut material + mixed lactic acid bacteria /
Composition C: Olive oil + Emulsifier + Fructo-oligosaccharide + mixed lactic acid bacteria

Example 2. Preparation of Emulsifier-Free Lactic Acid Bacteria Formulation B (Compositions: Table 1)

Composition B which does not contains the emulsifier and contains only sunflower oil (edible oil), five kinds of mixed lactic acid bacteria, and the rest of the additives (fructooligosaccharides and crushed peanut material) was prepared according to the same conditions as those described in Example 1 (Composition A) and used it as a test sample in the following Experimental Examples.

Example 3. Preparation of Comparative Lactic Acid Bacteria Formulation C

The composition C was prepared in the manner described in Example 1, but without the nut mixture.

Experimental Example 1. Preparation of Emulsion According to Various Heating Temperature 100 g of sunflower oil (vegetable oil, Sajo Daelim Co., Ltd.) was added with 2.0 g of emulsifier (glycerin fatty acid ester, ES food raw material) and heated to 4 different temperatures such as 40° C./60° C./85° C./100° C. The mixture was stirred and emulsified until the temperature of 4 to 10° C. was measured in a circulating cooling water bath (low temperature circulation constant temperature bath, SH-WB-7CDR) maintained at 0 to 4° C. to determine the optimum temperature suitable for the preparation of emulsion.

As a result of the experiment, as shown in FIG. 1, each photograph shows the shape of the emulsion formed by temperature, and at 40° C. and 60° C., the emulsifier was not sufficiently dissolved and the emulsion was not formed properly, but at 85° C. and 100° C., the emulsifier was sufficiently dissolved and the emulsion was evenly formed. (See FIG. 1: Emulsion Properties Experiment by Various Temperatures of Emulsifiers)

Experimental Example 2. Determination of Inventive Formulation on the Level of ADH (Alcohol Dehydrogenase) and ALDH (Aldehyde Dehydrogenase)

The effect of the lactic acid bacteria mixture composition A, composition B, composition C and comparative example (control group) on the activity of ADH (alcohol dehydrogenase) and acetaldehyde dehydrogenase (ALDH) was measured according to the modified method described in the existing literature (Roker, E., 1955, Alcohol dehydrogenase from baker's yeast, Methods Enzymol, 1, 500-506., Tottmar et al., 1973, The subcellular distribution and properties of aldehyde dehydrogenase in rat liver, Biochem. J. 135, 577-581).

The reagents used in the experiment were purchased from Sigma Corporation (MO, USA), and other analytical reagents were purchased from class 1 or higher ADH activity was measured by mixing 140 μl of distilled water, 75 μl of 1 M Tris-HCl buffer (pH 8.8), 30 μl of 20 mM NAD+, 30 μl of ethanol, and 10 μl of sample, and 15 μl of ADH in a 96-well plate for a total of 300 μl and reacting at 30° C. for 5 min. Afterwards, the change in absorbance was measured at 340 nm at 30 seconds intervals for 5 minutes. The control group was measured without the addition of the sample, and the activity was calculated as a relative ratio to the control group by the mathematical formula 1 {ADH activity (%)=(absorbance of the treatment group/absorbance of the control group)×100}.

For ALDH activity measurement, a mixture of 1 M Tris-HCl buffer (pH 8.0) 30 μl, 20 mM NAD+10 μl, 1 M acetaldehyde 10 μl, 3 M KCl 10 μl, 0.33 M 2-mercaptoehanol 10 μl, and 10 μl of sample was placed in a 96 well plate and 10 μl of ALDH was reacted at 30° C. for 5 min, and the absorbance change was measured at 340 nm at 30 sec intervals for 5 min. The control group was measured without the addition of the sample, and the activity was calculated as the relative ratio to the control group by the mathematical formula 2 {ALDH activity (%)=(absorbance of the treatment group/absorbance of the control group)×100}.

TABLE 2

| Determined activities of ADH and ALDH | | | | |
|---|---|---|---|---|
| enzyme | composition A | composition B | composition C | Control group (distilled water) |
| ADH activity (%) | 153 | 127 | 142 | 100 |
| ALDH activity (%) | 138 | 109 | 129 | 100 |

Figure 2:
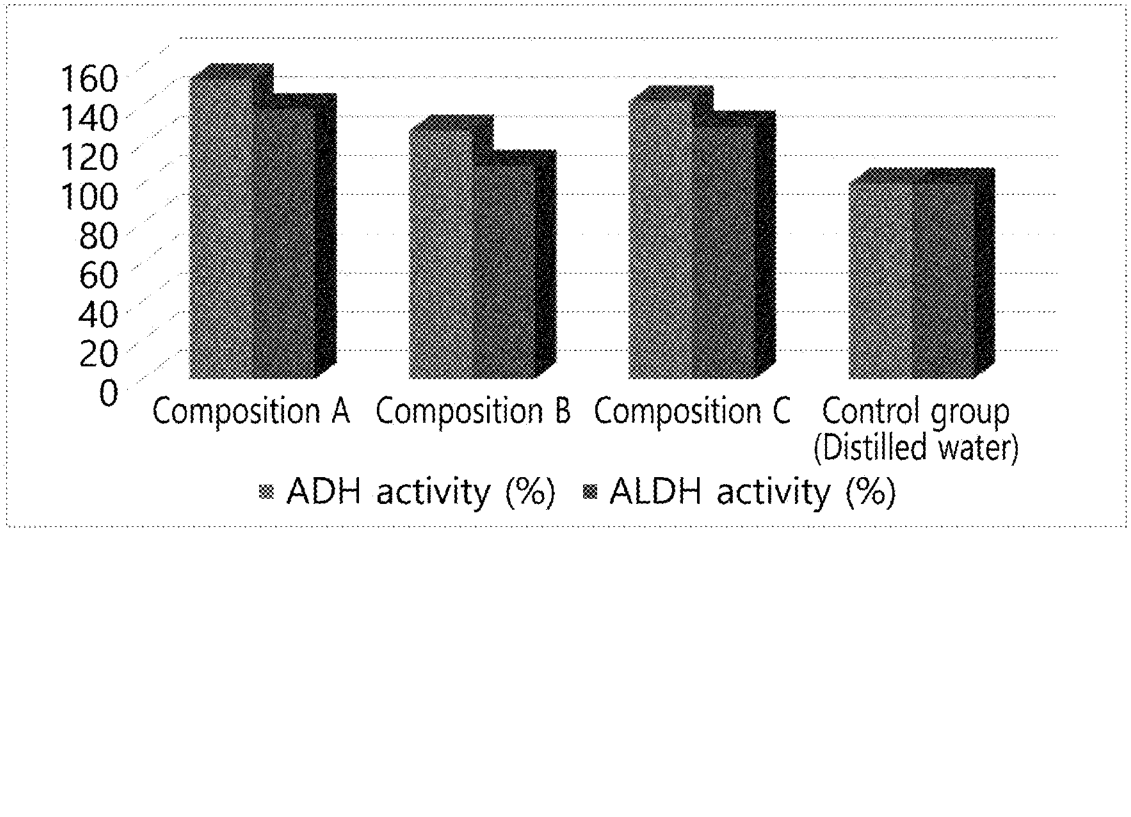
FIG. 2 represents the experimental results measuring Alcohol dehydrogenase (ADH) and Aldehyde dehydrogenase (ALDH)

As a result of the experiment, as can be seen from Table 2 and FIG. 2, the inventive composition A showed not only superior ADH and ALDH activity compared to the control group, but also showed the most excellent activity compared to composition C (including emulsifier, excluding nuts) and composition B (including nuts, excluding emulsifiers). Following composition A, it was found that composition C (including emulsifiers, excluding nuts) showed superior activity, and composition B (including nuts, excluding emulsifiers) showed better activity compared to the control group.

Experimental Example 3. Effect on the Viability of Lactic Acid Bacteria in Artificial Gastric Solution (pH 2)

In order to confirm the effect on the viability of lactic acid bacteria in artificial gastric solution (pH 2) of the sample of the present invention, the experiment was performed as follows according the method disclosed in the literature (Jeon et al., 2007, Identification and Characterization of Lactic Acid Bacteria Starters Isolated from the Commercial Drink-Yogurt Products, Korean J. Food Sci. Ani. Resour. 27(4), 509-516).

3-1. Experimental Strains and Procedure

In order to confirm the viability of lactic acid bacteria of the test samples, the composition A was stirred for a certain time (1 hour) in the artificial gastric solution (pH 2), and the collected composition was immediately cultured in a *Lactobacillus* selection medium (MRS agar plate, MB-M1024-P50, KisanBio) to incubate at 37° C., for 72±3 hours. The flat plate that formed 15-300 colonies per 1 plate was then selected and the number of colonies was calculated.

The number of strains was calculated by multiplying the measured colony number by the dilution multiple. For comparison, the composition which un-emulsified oil was mixed with a mixture of lactic acid bacteria, was used as a control group.

3-2. Test Result

As a result of the experiment, it can be observed that the mixture of emulsified oil and lactic acid bacteria is better than the survival rate of *Lactobacillus* in the control group. Moreover, when crushed peanut material was added to the emulsified oil as an additive and incubated under the same conditions, it has been confirmed that the survival rate of *Lactobacillus* in the *Lactobacillus* mixture containing more crushed peanut material was significantly better. (See Table 3 and FIG. 3)

TABLE 3

Test Results of Lactobacillus Viability Test in Artificial Gastric Fluid (pH 2)

| Constituent of compositions* | Number of strains |
|---|---|
| oil (O) + lactobacillus (L) mixture | $1.2 \times 10^2$ cfu/g |
| oil (O) + emulsifier (E) + lactobacillus (L) mixture | $1.7 \times 10^3$ cfu/g |
| oil (O) + emulsifier (E) + lactobacillus (L) mixture + crushed peanut material (P) | $2.4 \times 10^3$ cfu/g |

*Abbreviated: oil (O)/ emulsifier (E)/ lactobacillus (L)/ crushed peanut material (P)

Simple Clinical Test 1. Efficacy test of composition for reliving hangover syndrome After 50 healthy adult male volunteers in their 20~50s who had no abnormalities in alcohol metabolism were made to drink 200 ml of soju (alcohol concentration 16.5%) for 30 minutes, the test groups were divided into four groups, i.e., (1) the test group was made to consume 5 g of composition A, (2) the test group was made to consume 5 g of composition B, (3) the test group was made to consume 5 g of composition C, and (4) the control group was not consumed. A survey was conducted on the main hangover symptoms felt 12 hours after drinking. In the case of the main symptoms, there were many responses, but the most strongly felt hangover symptoms were chosen.

TABLE 4

Evaluation of the effectiveness of relieving hangover symptoms

| main hangover symptoms | | | | | |
|---|---|---|---|---|---|
| Class of syndrome | type | composition A | composition B | composition C | Control group |
| overall | fatigue, lethargy, thirst, | 3 | 6 | 5 | 10 |
| pain | headache, muscle pain | 5 | 4 | 3 | 8 |
| Gastrointestinal disorder | nausea, vomiting, stomach ache, diarrhea; | 2 | 5 | 5 | 7 |
| Sleeping & Circadian Rhythm | Loss of sleeping time catnap | 3 | 5 | 5 | 5 |
| Cognitive function | Deficit of attention/concentration | 2 | 3 | — | 5 |
| mood | depression, anxiety, keenness | — | — | 2 | — |
| Sympathetic nerve over-responsiveness | seizure sweating Increased pulse beat and blood pressure | — | — | — | 2 |
| No symptom | | 35 | 27 | 30 | 13 |
| sum | | 50 | 50 | 50 | 50 |

As can be seen from Table 4, the test group of the present invention shows that the relieving effect on various major hangover symptoms was significantly better than that of the control group. In particular, it was found that when prepared according to composition A, it showed the best hangover symptom relieving effect compared to composition C (including emulsifiers, excluding nuts) and composition B (including nuts, excluding emulsifiers). Following Composition A, Composition C (with emulsifiers, excluding nuts) showed excellent hangover symptom relief, and Composition B (including nuts, excluding emulsifiers) showed a better hangover symptom relief effect compared to the control group.

Simple Clinical Test 2. Determination of Alcohol Concentration (%) During Exhalation As with the simple clinical test 1, 10 healthy adult males in their 20~50s who do not have abnormalities in alcohol metabolism were divided into four groups, i.e., (1) the test group ingested 5 g of composition A, and was made to drink 200 ml of soju (alcohol concentration 16.5%) for 30 minutes; (2) the test group ingested 5 g of composition B and was made to drink 200 ml of soju (alcohol concentration 16.5%) for 30 minutes, (3) the test group ingested 5 g of composition C and was made to drink 200 ml of soju (alcohol concentration 16.5%) for 30 minutes (4) the test group ingested nothing and was made to drink 200 ml of soju (alcohol concentration 16.5%) for 30 minutes as a control group.

The alcohol concentration (%) during exhalation in four groups were determined for every 30 mins for 3 hours.

No water or other beverages were consumed from the beginning to the end of the experiment, and the alcohol concentration (%) during exhalation was measured using a commercially available portable breathalyzer (ALCOSCAN, AL8800), and the alcohol concentration (%) during each exhalation was the average value of the experimenters.

TABLE 5 alcohol concentration (%) during exhalation

| groups | The alcohol concentration (%) during exhalation: Before the experiment | 30 mins | 60 mins | 90 min | 120 mins | 150 mins | 180 mins |
|---|---|---|---|---|---|---|---|
| composition A | 0.000 | 0.043 | 0.038 | 0.033 | 0.019 | 0.004 | 0.000 |
| composition B | 0.000 | 0.054 | 0.049 | 0.043 | 0.033 | 0.018 | 0.004 |
| composition C | 0.000 | 0.047 | 0.040 | 0.037 | 0.025 | 0.013 | 0.000 |
| Control group | 0.000 | 0.062 | 0.059 | 0.051 | 0.042 | 0.029 | 0.015 |

Figure 4:
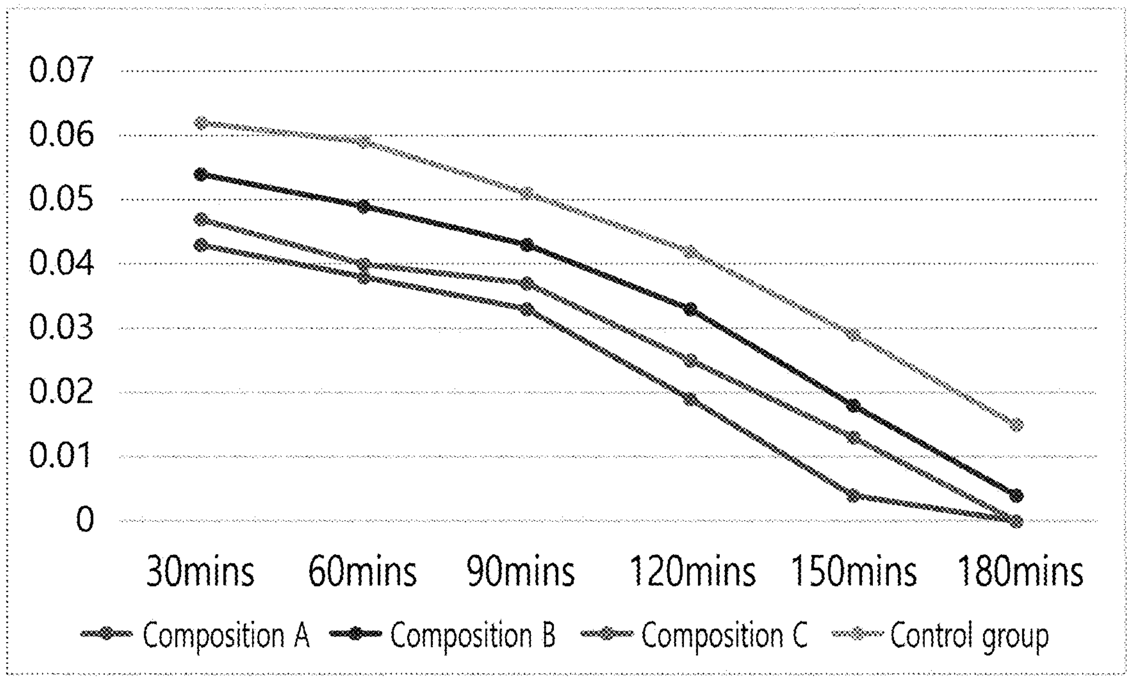
FIG. 4 presents the test result of measurement on the alcohol concentration (%) in exhalation of the lactic acid bacteria preparation of the present invention.

As can be seen from Table 5 and FIG. 4, the test group of the present invention have a better effect on reducing the alcohol concentration (%) during exhalation compared to the control group (% alcohol concentration reduction rate after 180 minutes: composition A: 100%, composition B: 92.6%, composition C: 100%, control group: 72.8%), and in particular, it can be seen that the time for alcohol to be broken down in the body was significantly reduced compared to the control group when drinking after ingestion of the inventive composition of the present invention.

In particular, it was found that composition A showed the best alcohol concentration reduction effect compared to composition C (including emulsifiers, excluding nuts) and composition B (including nuts, excluding emulsifiers). Following Composition A, Composition C (including emulsifiers, excluding nuts) showed an excellent alcohol concentration reduction effect, and Composition B (including nuts, excluding emulsifiers) showed a better alcohol concentration reduction effect compared to the control group.

As shown the test result, present inventors have confirmed that the lactic acid bacteria formulation of the present invention strongly exerts an excellent and advanced effect than the previously known lactic acid bacteria formulation through various experiments, for examples, (1) an experiment for the preparation of an emulsion solution by heating temperature (Experimental Example 1); Alcohol dehydrogenase (ADH) and Aldehyde dehydrogenase (ALDH) activity measurement experiment (Experimental Example 2); *Lactobacillus* viability experiment in artificial gastric juice (pH 2) (Experimental Example 3); Effect of inventive lactic acid bacteria formulation on the relieving hangover symptoms (simple clinical test 1); measurement on the alcohol concentration (%) in exhalation (simple clinical test 2), and it showed an excellent and advanced effect than the previously known lactic acid bacteria preparation in terms of hangover relief effect and liver function improvement effect as well as taste than the previously known lactic acid bacteria preparation.

Hereinafter, the formulating methods and kinds of excipients will be described, but the present invention is not limited to them. The representative preparation examples were described as follows.

Preparation of Powder

Composition A 20 mg
Lactose 100 mg
Talc 10 mg
Powder preparation was prepared by mixing above components and filling sealed package.

Preparation of Tablet

Composition A 10 mg
Corn Starch 100 mg
Lactose 100 mg
Magnesium stearate optimum amount
Tablet preparation was prepared by mixing above components and entabletting.

Preparation of Capsule

Composition A 100 mg
Crystalline cellulose 3 mg
Lactose 14.8 mg
Magnesium stearate 0.2 mg
capsule preparation was prepared by mixing above components and filling gelatin capsule by conventional gelatin preparation method.

Preparation of Injection

Composition A 10 mg
Mannitol 180 mg
Distilled water for injection 2974 mg
$Na_2HPO_4$, $12H_2O$ 26 mg
Injection preparation was prepared by filling all the components in 2 ㎖ sample and
sterilizing by conventional injection preparation method.

Preparation of Liquid

Composition A 20 mg
Sugar 10 g
Mannitol 180 mg
Distilled water
Liquid preparation was prepared by dissolving active component, and then filling all the components in 100 ㎖ ample and sterilizing by conventional liquid preparation method.

Preparation of Health Food

Composition A 1000 mg

Vitamin mixture optimum amount

Vitamin A acetate 70 g

Vitamin E1.0 mg

Vitamin $B_{10}$ 13 mg

Vitamin $B_2$ 0.15 mg

Vitamin $B_6$ 0.5 mg

Vitamin $B_{12}$ 0.2 g

Vitamin C 10 mg

Biotin 10 g

Amide nicotinic acid 1.7 mg

Folic acid 50 g

Calcium pantothenic acid 0.5 mg

Mineral mixture optimum amount

Ferrous sulfate 1.75 mg

Zinc oxide 0.82 mg

Magnesium carbonate 25.3 mg

Monopotassium phosphate 15 mg

Dicalcium phosphate 55 mg

Potassium citrate 90 mg

Calcium carbonate 100 mg

Magnesium chloride 24.8 mg

The above mentioned vitamin and mineral mixture may be varied in many ways. Such variations are not to be regarded as a departure from the spirit and scope of the present invention.

Preparation of Health Beverage

Composition A 1000 mg

Citric acid 1000 mg

Oligosaccharide 100 g

Apricot concentration 2 g

Taurine 1 g

Distilled water 900 ㎖

Health beverage preparation was prepared by dissolving active component, mixing, stirred at 85° C. for 1 hour, filtered and then filling all the components in 1000 ㎖ sample and sterilizing by conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

As described in the present invention, the present inventors have confirmed that the lactic acid bacteria formulation of the present invention strongly exerts an excellent and advanced effect than the previously known lactic acid bacteria formulation through various experiments, for examples, (1) an experiment for the preparation of an emulsion solution by heating temperature (Experimental Example 1); Alcohol dehydrogenase (ADH) and Aldehyde dehydrogenase (ALDH) activity measurement experiment (Experimental Example 2); *Lactobacillus* viability experiment in artificial gastric juice (pH 2) (Experimental Example 3); Effect of inventive lactic acid bacteria formulation on the relieving hangover symptoms (simple clinical test 1); measurement on the alcohol concentration (%) in exhalation (simple clinical test 2), and it showed an excellent and advanced effect than the previously known lactic acid bacteria preparation in terms of hangover relief effect and liver function improvement effect as well as taste than the previously known lactic acid bacteria preparation.

Therefore, the present invention can provides the therapeutics, functional health food or health care food for treating and preventing hangover or liver disease.

The invention claimed is:

1. A gastric acid-stable probiotic formulation for relieving hangover, comprising: (a) a mixed lactic acid bacteria; (b) sunflower seed oil; (c) glycerin fatty acid ester; and (d) a crushed peanut material, wherein the mixed lactic acid bacteria comprises *Lactobacillus acidophilus, Lactobacillus rhamnosus, Lactobacillus plantarum, Bifidobacterium longum*, and *Bifidobacterium animalis*, and wherein the crushed peanut material has a particle size of 0.01 to 0.1 mm.

2. The gastric acid-stable probiotic formulation according to claim 1, wherein a relative weight ratio of the (a) mixed lactic acid bacteria, the (b) sunflower seed oil, the (c) glycerin fatty acid ester, and the (d) crushed peanut material is 1.0 weight part: 1 to 90 weight parts: 0.1 to 5.0 weight parts: 5.0 to 90.0 weight parts, respectively.

3. The gastric acid-stable probiotic formulation according to claim 1, wherein the gastric acid-stable probiotic formulation further comprises one or more additional ingredients selected from the group consisting of a prebiotic, and a cohesive agent.

4. The gastric acid-stable probiotic formulation according to claim 3, wherein a relative weight ratio of the (a) mixed lactic acid bacteria, the (b) sunflower seed oil, the (c) glycerin fatty acid ester, the (d) crushed peanut material, the (e) prebiotic, and the (f) cohesive agent is 1.0 weight part: 1 to 90 weight parts: 0.1 to 5.0 weight parts: 5.0 to 90.0 weight parts: 0.01 to 5.0 weight parts: 0.1 to 5.0 weight parts, respectively.

5. The gastric acid-stable probiotic formulation according to claim 4, wherein the (e) prebiotic is fructo-oligosaccharide.

6. The gastric acid-stable probiotic formulation according to claim 4, wherein the (f) cohesive agent is xanthan gum.

7. A health care food comprising the gastric acid-stable probiotic formulation according to claim 1 for the prevention or alleviation of hangover or liver disease.

8. A food additive comprising the gastric acid-stable probiotic formulation according to claim 1 for the prevention or alleviation of hangover or liver disease.

9. A health functional food comprising the gastric acid-stable probiotic formulation according to claim 1 as an active ingredient to improve or prevent hangover or liver disease.

10. The health functional food according to claim 9, wherein the health functional food is provided as a powder, a granule, a tablet, a chewing tablet, a capsule, or a beverage form.

11. A pharmaceutical composition comprising the gastric acid-stable probiotic formulation according to claim 1 as an active ingredient to treat or prevent hangover or liver disease.

12. The pharmaceutical composition according to claim 11, wherein said liver disease is selected from autoimmune liver disease, drug-induced liver disease, alcoholic liver disease, non-alcoholic liver disease, infectious liver disease, congenital metabolic liver disease, acute hepatitis, chronic hepatitis, liver cirrhosis, liver sclerosis, fatty liver or liver cancer.

* * * * *